US009131944B2

(12) United States Patent
Gavriely et al.

(10) Patent No.: US 9,131,944 B2
(45) Date of Patent: Sep. 15, 2015

(54) MOBILE TORUS DEVICES

(75) Inventors: Noam Gavriely, Haifa (IL); Oren Gavriely, Haifa (IL); Benny Rousso, Rishon-LeZion (IL)

(73) Assignee: OHK MEDICAL DEVICES LTD., Haifa (IL)

( * ) Notice: Subject to any disclaimer, the term of this patent is extended or adjusted under 35 U.S.C. 154(b) by 1825 days.

(21) Appl. No.: 12/361,557

(22) Filed: Jan. 29, 2009

(65) Prior Publication Data

US 2009/0248061 A1    Oct. 1, 2009

Related U.S. Application Data

(60) Provisional application No. 61/006,728, filed on Jan. 29, 2008.

(51) Int. Cl.
*A61B 17/00* (2006.01)
*A61B 17/132* (2006.01)
*A61B 17/135* (2006.01)

(52) U.S. Cl.
CPC ......... *A61B 17/1322* (2013.01); *A61B 17/1355* (2013.01)

(58) Field of Classification Search
CPC ............. A61B 17/132; A61B 17/1322; A61B 17/135; A61B 17/1355
USPC .......................... 606/201–204; 600/490–499; 601/118–121
See application file for complete search history.

(56) References Cited

U.S. PATENT DOCUMENTS

| 34,112 | A | 1/1862 | Lambert |
|---|---|---|---|
| 35,038 | A | 4/1862 | Pierce |
| 800,467 | A | 9/1905 | Myers |
| 814,795 | A | 3/1906 | Myers |
| 1,279,784 | A | 3/1914 | Stöpler et al. |
| 2,149,149 | A | 2/1939 | Scheinberg |
| 2,320,179 | A | 5/1943 | Gray |
| 2,333,237 | A | 11/1943 | Iteksoiii |
| 2,574,873 | A | 11/1951 | Jobst |
| 2,582,648 | A | 1/1952 | Mpwbray |
| 2,604,098 | A | 7/1952 | Kranc |
| 2,796,207 | A | 6/1957 | Young |
| 3,095,873 | A | 7/1963 | Edmunds |

(Continued)

FOREIGN PATENT DOCUMENTS

| BG | 99835 U | 3/1997 |
|---|---|---|
| CN | 1602170 | 3/2005 |

(Continued)

OTHER PUBLICATIONS

PCT Search Report for PCT/IL2002/00992 transmitted.

(Continued)

*Primary Examiner* — Katherine Rodjom
(74) *Attorney, Agent, or Firm* — Dvorah Graeser; Graeser Associates International Inc

(57) ABSTRACT

Disclosed is a device for exsanguinating a portion of an extremity, the device comprising a torus having a variable circumferential diameter, the torus configured to encircle an extremity portion and apply exsanguination pressure thereto, and a transducer operatively associated with the torus, the transducer, while the torus is encircling the extremity portion, being configured to control at least one of a diameter of the variable circumferential diameter, a tension in the torus and a pressure applied by the torus.

22 Claims, 10 Drawing Sheets

(56) References Cited

U.S. PATENT DOCUMENTS

| | | |
|---|---|---|
| 3,097,644 A | 7/1963 | Parker |
| 3,227,335 A | 1/1966 | Minnema |
| 3,279,459 A | 10/1966 | Schenker |
| 3,454,010 A | 7/1969 | Lilligren |
| 3,935,984 A | 2/1976 | Lichowsky |
| 3,968,792 A | 7/1976 | Small |
| 4,206,765 A | 6/1980 | Huber |
| 4,243,039 A | 1/1981 | Aginsky |
| 4,441,504 A | 4/1984 | Peterson |
| 4,479,494 A | 10/1984 | McEwen |
| 4,520,820 A | 6/1985 | Kitchin |
| 4,548,198 A | 10/1985 | Manes |
| 4,566,436 A | 1/1986 | Loefqvist |
| 4,577,622 A | 3/1986 | Jennings |
| 4,637,394 A | 1/1987 | Racz |
| 4,738,249 A | 4/1988 | Linman |
| 4,765,520 A | 8/1988 | Barton |
| 4,770,175 A | 9/1988 | McEwen |
| 4,848,324 A | 7/1989 | Gavriely |
| 4,869,265 A | 9/1989 | McEwen |
| 4,872,463 A | 10/1989 | Nishizeno |
| 4,972,850 A | 11/1990 | Broad, Jr. |
| 4,980,150 A | 12/1990 | Keith |
| 5,048,536 A | 9/1991 | McEwen |
| 5,163,448 A | 11/1992 | Foldesy |
| 5,181,522 A | 1/1993 | McEwen |
| 5,193,549 A | 3/1993 | Bellin |
| 5,203,786 A | 4/1993 | Vernick |
| 5,226,874 A | 7/1993 | Heinz |
| 5,304,202 A * | 4/1994 | Stahl ............................ 606/203 |
| 5,312,431 A | 5/1994 | McEwen |
| 5,351,694 A | 10/1994 | Davis |
| 5,351,698 A | 10/1994 | Wheeler |
| 5,376,067 A | 12/1994 | Daneshvar |
| 5,383,893 A | 1/1995 | Daneshvar |
| 5,411,518 A | 5/1995 | Goldstein |
| 5,413,582 A | 5/1995 | Eaton |
| 5,454,831 A | 10/1995 | McEwen |
| 5,556,073 A | 9/1996 | Wawro |
| 5,578,055 A | 11/1996 | McEwen |
| 5,582,689 A | 12/1996 | Van Haag |
| 5,606,982 A | 3/1997 | Piotti |
| 5,607,448 A | 3/1997 | Stahl |
| 5,620,001 A | 4/1997 | Byrd |
| 5,649,954 A | 7/1997 | McEwen |
| 5,669,390 A | 9/1997 | McCormick |
| 5,695,513 A | 12/1997 | Johnson |
| 5,695,520 A | 12/1997 | Bruckner |
| 5,741,295 A | 4/1998 | McEwen |
| 5,876,436 A | 3/1999 | Vanney |
| 5,893,871 A | 4/1999 | Tanaka |
| 6,149,666 A | 11/2000 | Marsden |
| 6,361,496 B1 | 3/2002 | Zikorus |
| 6,682,547 B2 | 1/2004 | McEwen |
| 6,746,470 B2 | 6/2004 | McEwen |
| 7,077,814 B2 | 7/2006 | Mollenauer |
| 7,604,651 B1 | 10/2009 | Harris |
| 7,854,941 B2 | 12/2010 | Urban |
| 2001/0020176 A1* | 9/2001 | Mach ............................ 606/201 |
| 2003/0065357 A1 | 4/2003 | Dedo |
| 2003/0139766 A1 | 7/2003 | McEwen et al. |
| 2004/0111047 A1 | 6/2004 | Reid |
| 2005/0080450 A1 | 4/2005 | Gavriely |
| 2005/0087573 A1 | 4/2005 | Unsworth |
| 2005/0113866 A1 | 5/2005 | Heinz |
| 2005/0143766 A1* | 6/2005 | Bachmann et al. ............ 606/158 |
| 2005/0159688 A1* | 7/2005 | Sakamoto et al. ............. 601/123 |
| 2005/0267518 A1 | 12/2005 | Wright |
| 2006/0025807 A1 | 2/2006 | Licata |
| 2007/0191881 A1 | 8/2007 | Amisar |
| 2008/0081020 A1 | 4/2008 | Huang |
| 2008/0262533 A1* | 10/2008 | McEwen et al. ............... 606/202 |

FOREIGN PATENT DOCUMENTS

| | | |
|---|---|---|
| EP | 1453424 | 9/2004 |
| EP | 1453434 | 9/2004 |
| GB | 206271 | 11/1923 |
| GB | 713132 | 8/1954 |
| JP | 59-183216 U | 12/1984 |
| JP | 2001161742 | 6/2001 |
| WO | WO2005079691 | 9/2005 |
| WO | WO2006071251 | 7/2006 |

OTHER PUBLICATIONS

Office Action dated Sep. 19, 2007 for AU application 2002360196.
Crenshaw et al, Wide tourniquets cuff more effective at lower inflation pressures, Acta Orthopaedica, Aug. 1, 1988, pp. 447-451, vol. 59 No. 4.
Office Action dated Mar. 17, 2010 for CA application 2469283.
Office Action dated Dec. 26, 2008 for JP application 2003-550674.
PCT Search Report for PCT/IL2002/00992.
Office Action dated Jan. 15, 2009 for IN application 1287/CHENP/2004.
Office Action dated Sep. 16, 2005 for CN application 02824809.0.

* cited by examiner

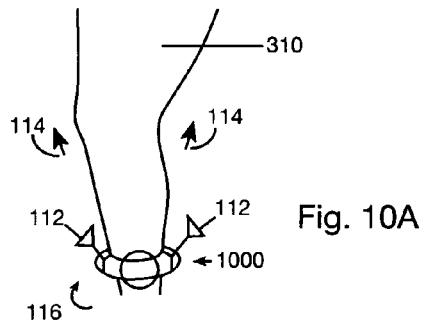
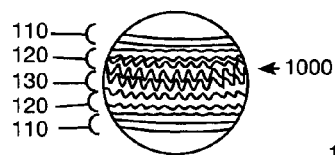
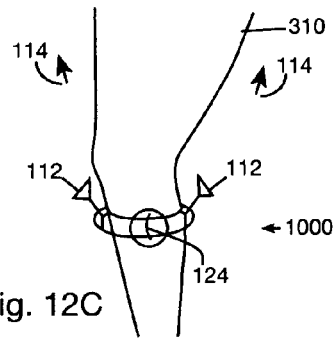
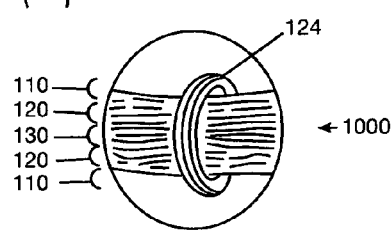
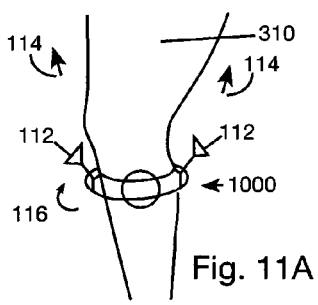
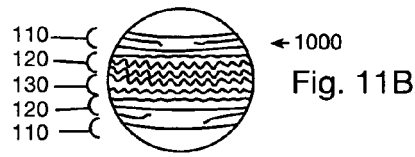
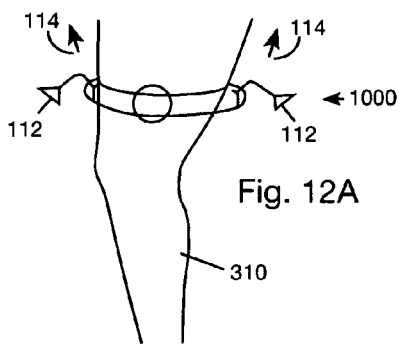
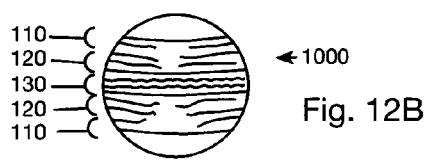

MOBILE TORUS DEVICES

RELATED APPLICATIONS

The present application claims the benefit of U.S. Provisional Patent Application No. 61/006,728, filed on Jan. 29, 2008, the disclosure of which is incorporated herein by reference.

FIELD AND BACKGROUND OF THE INVENTION

The present invention, in some embodiments thereof, relates to mobile torus devices and, more particularly, but not exclusively, to mobile torus devices and methods for exsanguinating an extremity.

A bloodless extremity during a surgical procedure is highly desirable in helping the surgeon identify tissue layers, anatomic landmarks and biological structures.

To attempt to exsanguinate the extremity and render a bloodless surgical site, a first sterile assistant typically elevates the extremity above the heart while a second sterile assistant wraps an elastic bandage in a spiral fashion from the distal portion of the extremity to proximal to the surgical site.

The elastic wrap drives some of the blood in the extremity proximal to the surgical site and, to prevent a flow of blood during surgery, a pneumatic tourniquet proximal to the surgical site, is inflated to a pressure of between 150 and 500 millimeters of mercury (mm Hg).

The elastic bandage is then removed and the surgeon makes a first incision into the surgical site.

The first incision, however, is often accompanied by a release of residual blood remaining in the extremity distal to the tourniquet. The residual blood often covers and obstructs visualization of the surgical site. Lavage and copious sponging by a sterile assistant renders a relatively bloodless, but wet, surgical site.

U.S. patent application Ser. No. 10/498,369, now published as U.S. Patent Application Publication No. 20051008045O Al (Gavriely) teaches a tubular sock and elastic annulus that are rolled along the extremity to exsanguinate the extremity.

SUMMARY OF THE INVENTION

According to one aspect of some embodiments of the invention, there is provided a device for exsanguinating a portion of an extremity, the device comprising a torus having a variable circumferential diameter, the torus configured to encircle an extremity portion and apply exsanguination pressure thereto, and a transducer operatively associated with the torus, the transducer, while the torus is encircling the extremity portion, being configured to control at least one of a diameter of the variable circumferential diameter, a tension in the torus and a pressure applied by the torus.

According to some embodiments of the invention, during the moving the transducer is additionally configured to control the variable circumferential diameter of the torus.

According to some embodiments of the invention, during the moving the transducer is configured to apply a substantially constant exsanguinating pressure to the extremity portion.

According to some embodiments of the invention, the torus is configured to move along the extremity portion with at least one of twisting rotation, and sliding.

According to some embodiments of the invention, the torus includes at least one wheel located around a cross sectional section of an annular portion of the torus, the at least one wheel and configured to roll along the extremity portion as the torus is moved.

According to some embodiments of the invention, an outer surface of the at least one wheel comprises at least two projections configured to contact at least a portion of the extremity portion.

According to some embodiments of the invention, the at least one wheel, comprises at least two wheels, one first wheel configured to slidingly engage at least one second wheel.

According to some embodiments of the invention, the torus includes at least one pulling handle configured to pull the torus along the extremity portion.

According to some embodiments of the invention, the at least one pulling handle is rotatably connected to the torus.

According to some embodiments of the invention, the torus includes at least one motor configured to propel the torus during the moving.

According to some embodiments of the invention, the transducer comprises at least two bands of fibers at least partially encircling the torus, the at least two bands of fibers including at least one first band of fibers having a first rate of elasticity, and at least one second band of fibers having a second rate of elasticity.

According to some embodiments of the invention, the at least one first band of fibers break when stretched above the first rate of elasticity, and the at least one second band of fibers break when stretched above the second rate of elasticity.

According to some embodiments of the invention, the torus includes at least one pulling handle configured to pull the torus along the extremity portion.

According to some embodiments of the invention, the torus includes at least one motor configured to propel the torus during the moving.

According to some embodiments of the invention, the transducer comprises at least one of at least one variably extendable tension band, at least one variably inflatable ballast, at least one spring, at least one hydraulic piston and at least two sections of a diaphragm.

According to some embodiments of the invention, the transducer includes a tension controller including a tension level input.

According to some embodiments of the invention, the tension level input comprises a wireless transceiver configured to receive and transmit wireless tension-based signals.

According to some embodiments of the invention, the torus includes at least one pulling handle configured to pull the torus along the extremity portion.

According to some embodiments of the invention, the torus includes at least one motor configured to propel the torus during the moving.

According to some embodiments of the invention, the at least one variably inflatable ballast is substantially contained within a cross sectional portion of the torus.

According to some embodiments of the invention, the at least one spring comprises at least one spring assembly including at least one of: dual constant rate springs, a dual variable rate spring, and a triple variable rate spring.

According to some embodiments of the invention, the at least one spring assembly includes at least one spring attenuator including at least one magnetic field.

According to another aspect of some embodiments of the invention, there is provided a method for exsanguinating an extremity portion, the method including: providing a torus having a variable circumferential diameter, the torus configured to encircle a cross sectional annulus of an extremity portion, moving the torus along the extremity portion, and applying a substantially constant exsanguinating pressure with the torus to the extremity during the moving.

According to some embodiments of the invention, the torus includes one variable circumferential diameter adjuster configured to apply the substantially constant exsanguinating pressures to the extremity portion, the one variable circumferential diameter adjuster including at least one of: a constant rate spring, a dual variable rate spring, a triple variable rate spring, a variable length band, a variable rate piston, a variably inflatable ballast, at least two encircling bands of fibers having variable rates of elongation, and at least two sections of a diaphragm.

According to some embodiments of the invention, the moving of the torus along the extremity portion comprises at least one of twisting rotation, rolling, and sliding.

According to a further embodiment of the invention, there is provided a device for maintaining exsanguination of a portion of an extremity, the device including a torus including a variably inflatable ballast, and a variable ballast inflator substantially contained within a cross sectional portion of the torus.

According to some embodiments of the invention, the variably inflatable ballast is substantially contained within a cross sectional portion of the torus.

According to some embodiments of the invention, the variable ballast inflator includes a tension sensor.

According to some embodiments of the invention, the tension sensor is substantially contained within a cross sectional portion of the torus.

According to some embodiments of the invention, the variable ballast inflator includes a wireless transceiver configured to receive and transmit inflation-based signals.

The present invention successfully addresses the shortcomings of the presently known configurations by providing mobile torus exsanguination devices and methods.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques and procedures for accomplishing a given task including, but not limited to, those manners, means, techniques and procedures either known to, or readily developed from known manners, means, techniques and procedures by practitioners of orthopedic biomechanics.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 10A-B, 11A-B and 12A-D show configurations of a varied fiber mobile torus being deployed on an extremity, according to embodiments of the invention.

DESCRIPTION OF EMBODIMENTS OF THE INVENTION

Figure 1:
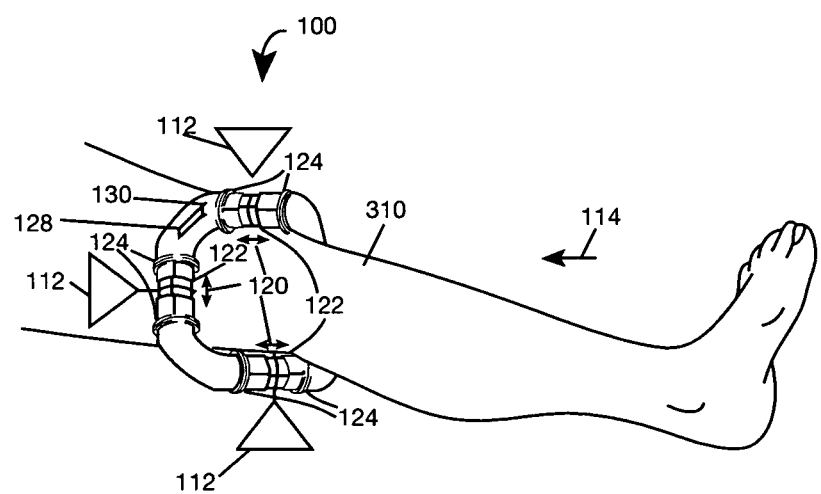
FIG. 1 shows a mobile torus being deployed on an extremity, according to embodiments of the invention.

The present invention, in some embodiments thereof, relates to mobile torus devices and, more particularly, but not exclusively, to mobile torus devices and methods for exsanguinating an extremity.

Disclosed is a mobile torus configured to surround and move along an extremity portion while applying a constant exsanguinating pressure. During proximal movement, blood in the extremity is pushed proximal to the mobile torus so that the extremity distal to the mobile torus becomes substantially blood free. The mobile torus is then positioned proximal to the surgical site, maintaining the exsanguination and allowing a surgeon work in a bloodless field following incision of the surgical site.

According to some embodiments of the invention, the torus has a variable circumferential diameter and adjusts diameter according to the thickness of the extremity the mobile torus passes over, thereby maintaining a constant exsanguination pressure while moving along and/or encircling the extremity.

In some embodiments, the mobile torus comprises sliding sections that are maintained in tension and slide one into the other to provide constant exsanguination pressure.

In some embodiments, an adjustable electronically extendable tension band, set to a designated pressure, automatically adjusts the tension and/or extension of the sliding sections to provide constant pressure over thicker or thinner cross sectional areas of the extremity.

There are a variety of additional mechanisms contemplated for adjusting the tension in the sliding sections and/or the diameter of the torus. For example, in some embodiments, variable rate springs are secured within the torus along the sliding sections. The tension provided by the variable rate springs may be pre-set during manufacture or controlled by a controller comprising, for example, a magnetic field.

In other embodiments, hydraulic pistons internal to the torus that are electronically controlled by a tension-adjusting controller provide the necessary tension in the sliding sections and/or varying the diameter of the torus. Optionally, the tension-adjusting controller includes a tension set input allowing an operator to set the tension in the torus. In still other embodiments, the tension-adjusting controller includes a wireless transceiver that receives and/or transmits tension information.

In still other embodiments, the tension mechanism includes a variably inflatable ballast having inflation and deflation pumps that control the pressure in the torus. Greater pressure decreases the internal circumferential diameter of the torus, so that the torus maintains constant exsanguination pressure around thin cross sections of the extremity.

Conversely, as the torus is moved for example, from a thinner knee to a thicker thigh portion, the deflation pump partially deflates the torus to maintain substantially the same exsanguination pressure around the thigh as around the knee.

In still further embodiments, the mobile torus comprises multiple fibers arranged circumferentially around portions of the torus, each fiber having a different elasticity threshold above which the fiber breaks. At the distal narrow portion of the extremity, all fibers remain intact, providing the smallest diameter at a given pressure on the extremity.

As the mobile torus is moved proximally along the extremity and reaches a thicker portion, for example in moving from the ankle to the calf, a first set fibers having a lower elasticity threshold break, allowing the torus to attain a larger diameter against the calf while maintaining the same pressure as that of the ankle.

As the torus passes proximal to the knee a second set of fibers having a higher elasticity threshold, break. A third set of fibers having an even higher elasticity threshold remain patent, allowing the mobile torus to increase in diameter while maintaining constant pressure around the thigh.

In some embodiments, the mobile torus twistingly rotates to move along the extremity. In further embodiments, the mobile torus includes wheels encircling annular portions of the torus and the wheels rotate while contacting the extremity and while the mobile torus is moved along the extremity.

Optionally, the wheels are mechanized with rotation-providing transducers, for example one or more motors, and the mobile torus moves along the extremity without requiring manual exertion by a user.

In still further embodiments, the mobile torus comprises a substantially friction free surface that contacts the extremity and the mobile torus slides along the extremity with or without additional lubrication.

The principles and operation of mobile torus exsanguination devices and methods according to the present invention may be better understood with reference to the drawings and accompanying descriptions.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

In some embodiments of the present invention, variable diameters of a torus may provide effective constant exsanguination pressure. The following embodiment provides just one such variable diameter option.

Referring Now to the Drawings:

FIG. 1 shows a mobile torus 100 having a variable radius provided by sliding sections 122 that provide resistance against enlargement of the diameter of mobile torus 100, thereby providing constant pressure.

Mobile torus 100 is shown being pulled over a portion of an extremity while providing exsanguinating pressure to extremity 310. While moving in a proximal direction 114, mobile torus 100 presses extremity 310 so that blood moves distal to mobile torus 100, leaving the proximal portion of extremity 310 substantially bloodless.

According to some embodiments of the invention, mobile torus 100 comprises multiple wheels 124 that rotate along extremity 310 to facilitate movement as mobile torus 100 is pulled proximally in direction 114 using handles 112. According to some embodiments of the invention, handles 112 are rotatingly attached to mobile torus 100.

In alternative embodiments, explained below, mobile torus 100 without wheels 124 can be twistingly rotated along extremity 310. In still further embodiments, mobile torus 100 may be configured to slide along extremity 310 while one portion of mobile torus 100 is constantly in contact with extremity 310.

According to some embodiments of the invention, to provide constant exsanguinating pressure, mobile torus 100 comprises sliding sections 122 that provide resistance against enlargement of the diameter of mobile torus 100. Sliding sections 122 extendably adjust to change the diameter and compensate for thicker or thinner portions of extremity 310.

As a result of extendably adjusting, mobile torus 100 circumferentially compresses the tissue of extremity 310 with constant pressure, no matter the thickness of extremity 310. With movement in direction 114, mobile torus 100 provides the above-noted movement of blood proximal to mobile torus 100.

Mobile torus 100 can comprise any number of circumferential adjusting mechanisms to maintain constant pressure against extremity 310, some of while will now be explained.

Tension Band Mechanism

Figure 2:
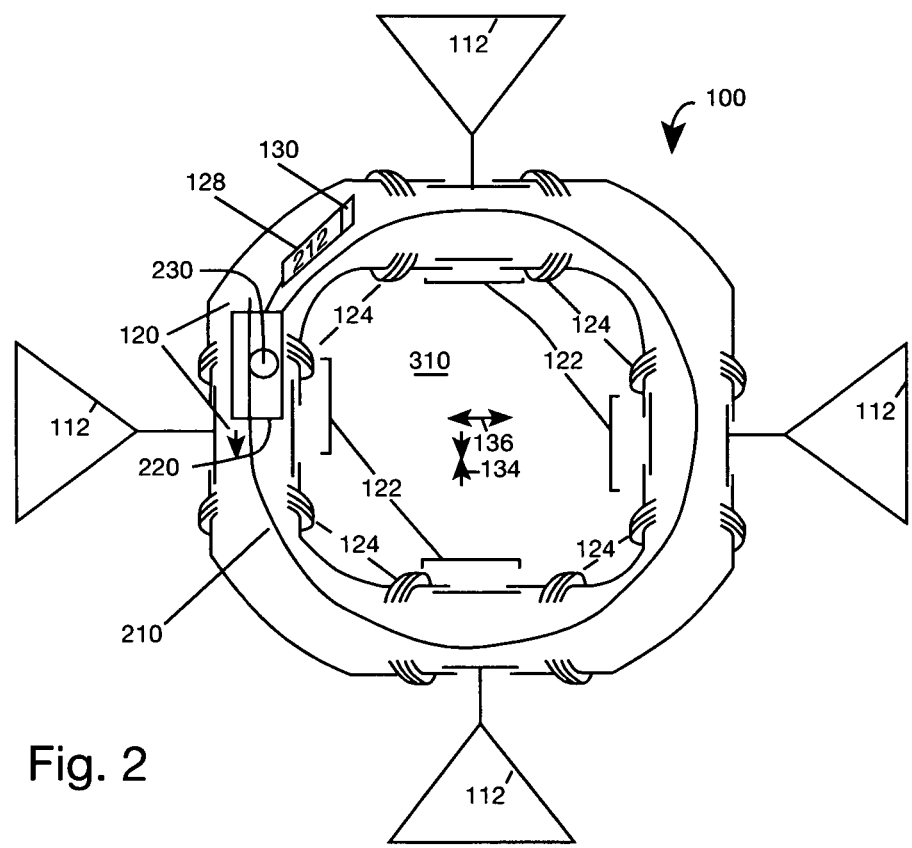
FIG. 2 shows the mobile torus of FIG. 1 in cross section, according to embodiments of the invention.

FIG. 2 shows mobile torus 100 in cross section wherein an optional tension band 210 continually changes the diameter of mobile torus 100 to maintain constant pressure.

In embodiments, the tension of tension band 210 is continually adjusted by a tension adjuster 220, thereby changing the diameter of mobile torus 100. Within tension adjuster 220, a tensioning wheel 230 rotates to pull tension band 210 so that sliding sections 122 compact to decrease the diameter of mobile torus 100 in a direction 134. Alternatively, tensioning wheel 230 rotates to releases tension on tension band 210 so that sliding sections 122 extend and increase the diameter of mobile torus 100 in a direction 136.

Prior to applying mobile torus 100 the user sets an exsanguinating pressure on a display 128 by pressing a button 130 to advance the numbers on display 128 to a specific amount of exsanguinating pressure. While display 128 shows that the pressure will be maintained at 212 mm Hg, any amount of pressure may be set; typically being between 150 and 500 mm Hg noted above.

In some embodiments of the present invention, there are alternative configurations that can provide effective adjustment to the changing topology of an extremity. The following embodiment provides just one such alternative configuration.

Alternative Torus Configurations

Figure 3A:
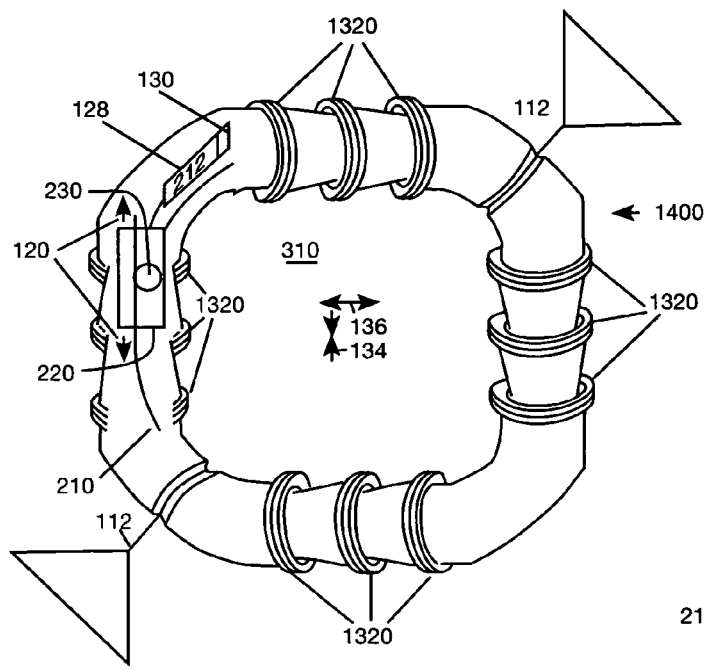
FIGS. 3A-3C show alternative wheel configurations for the mobile torus of FIG. 1, according to embodiments of the invention.

In some embodiments positioning of handles 112 and/or number of handles 112 are optionally varied according to the needs of specific circumstances. For example, as shown in FIG. 3A, two handles 112 are provided so that a single operator can operate torus 1400 during exsanguination.

Figure 3B:
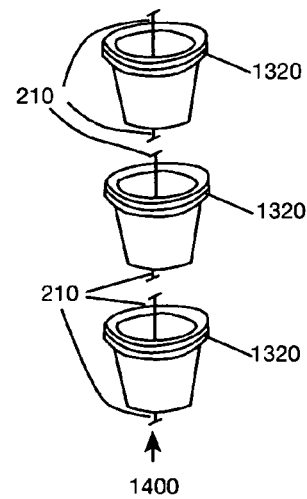

In embodiments, handles 112 are rotatingly located at the corners of mobile torus 100. Additionally or alternatively, as seen in detail in FIG. 3B, mobile torus 100 comprises multiple tapered wheel sections 1320 that slide into one another. Tapered wheel sections 1320 may have application in moving over damaged skin, for example due to burn injuries, with the pressure of mobile torus 100 spread over a larger surface area to possibly aid in preventing further damage to the delicate skin.

Figure 3C:
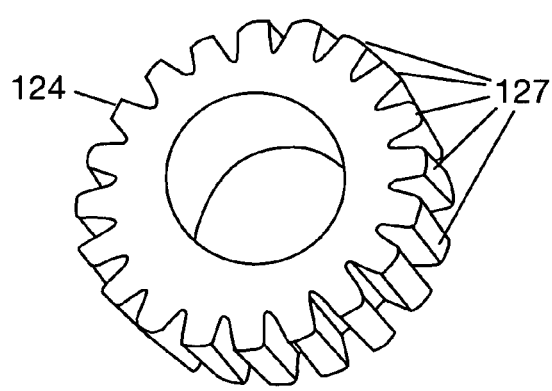

FIG. 3C shows a ratcheted wheel 124, having multiple projections 127 optionally made of a soft material that may be incorporated into tapered wheel section 1320 to provide additional friction for moving mobile torus 100.

In some embodiments of the present invention, there are alternative configurations to tension band 210 described above. The following spring embodiments provide just a few of many such alternative configurations.

Constant Rate Spring Torus

In some embodiments, the diameter and/or tension of an exsanguinating torus may adjusted by a non-mechanized tension adjuster.

Figure 4:
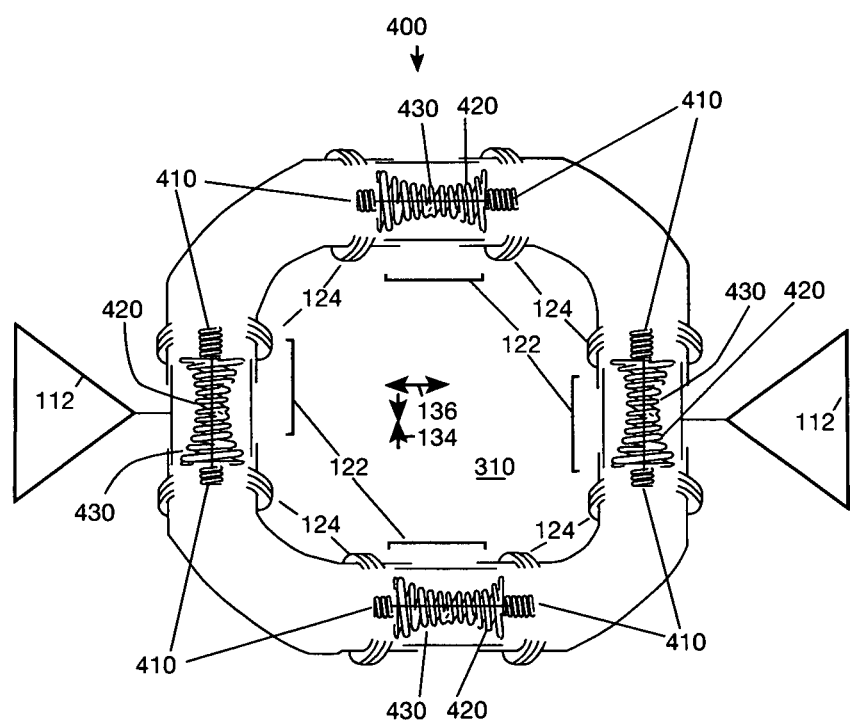
FIGS. 4-7 show alternative configurations of the mobile torus of FIG. 1, according to embodiments of the invention.

FIG. 4 shows one example of a non-mechanized tension adjuster in which a mobile torus 400 includes dual constant rate spring assemblies 420 that are preset to allow sliding sections 122 to compact or extend while maintaining constant exsanguination pressure. Dual rate springs comprise tightly wound light gage central coils 410 and loosely wound high gage outer coils 430.

When mobile torus 400 passes over an extremity portion having a smaller diameter, both light gage central coils 410 and high gage outer coils 430 maintain extension of sliding sections 122, providing constant exsanguinating pressure.

As mobile torus 400 passes over a thicker extremity portion, light gage central coils 410 are stretched to a maximum and high gage outer coils 430 maintain extension of sliding sections 122, providing constant exsanguinating pressure.

According to some embodiments of the invention, high gage outer coils 430 and light gage central coils 410 are manufactured to provide a single constant compression. There are a variety to mechanisms that can allow a user to adjust a spring assembly to provide different amounts of exsanguination, one of which will now be explained.

Dual Variable Rate Spring Torus

Variable rate springs are optionally provided in conjunction with mechanized tension adjusters that adjust tension in a torus.

Figure 5:
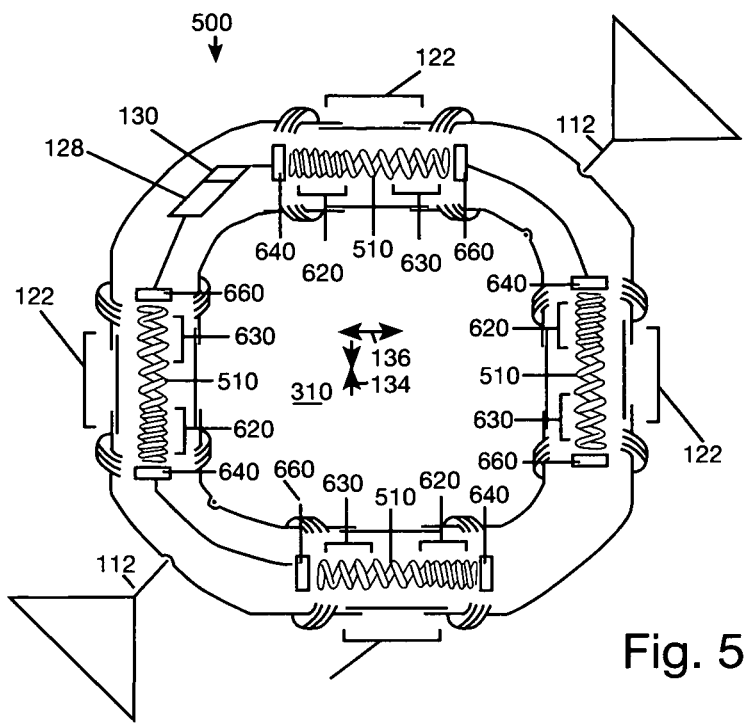

One example of mechanized tension adjusters is seen in FIG. 5, wherein a dual variable rate spring torus 500 includes dual variable rate springs 510.

According to some embodiments of the invention, dual variable rate springs 510 comprise light gage coils 620 connected to medium gage coils 630, which maintain compression over a smaller extremity cross section. As dual variable rate spring torus 500 passes over a thicker extremity portion, light gage coils 620 are stretched to a maximum and medium gage coils 630 maintain extension of sliding sections 122, providing constant exsanguinating pressure.

According to some embodiments of the invention, dual variable rate spring torus 500 includes electromagnets 640 and 660 that attract or repel each other to adjust the compression across variable rate springs 510 to provide a constant exsanguinating pressure to extremity 310.

As noted above, display 128 can be adjusted by a user to provide a specific constant exsanguinating pressure to extremity 310.

Triple Variable Rate Spring Torus

The use of springs that provide tension adjustments is not limited to dual rate springs. For example, optionally the spring mechanisms include any number of springs having varied rates of expansion.

Figure 6:
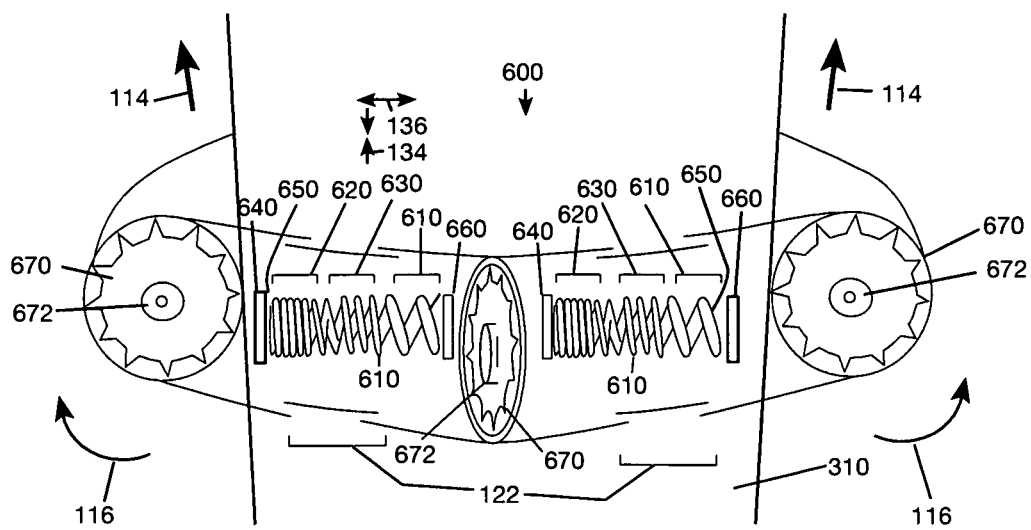

Just one example of springs having more than two rates of expansion is shown in FIG. 6 in which a triple rate spring torus 600 including triple variable rate spring assemblies 610 which include a third extra heavy gage section 650. Exsanguinating pressure over a smaller extremity cross section is maintained with light gage 620, medium gage 630 and heavy gage 650 springs.

As triple variable rate spring torus 600 passes over a medium thick extremity portion, light gage coils 620 are stretched to a maximum and medium gage coils 630 and heavy gage coils 650 maintain extension of sliding sections 122, providing constant exsanguinating pressure.

Over a thick extremity portion, both light gage coils 620 and medium gage coils 630 are stretched to a maximum, and medium 630 and heavy gage coils 650 maintain extension of sliding sections 122, providing constant exsanguinating pressure.

According to some embodiments of the invention, mobile torus 600 includes wheels 670 that are powered by motors 672 so that mobile torus 600 is self-propelled in direction 114 or in the reverse direction when exsanguination is no longer required, for example following the surgical procedure.

In some embodiments of the present invention, there are alternative configurations to spring-provided constant pressure. The following hydraulic embodiment provides just one example of such an alternative configuration.

Hydraulic Torus

Figure 7:
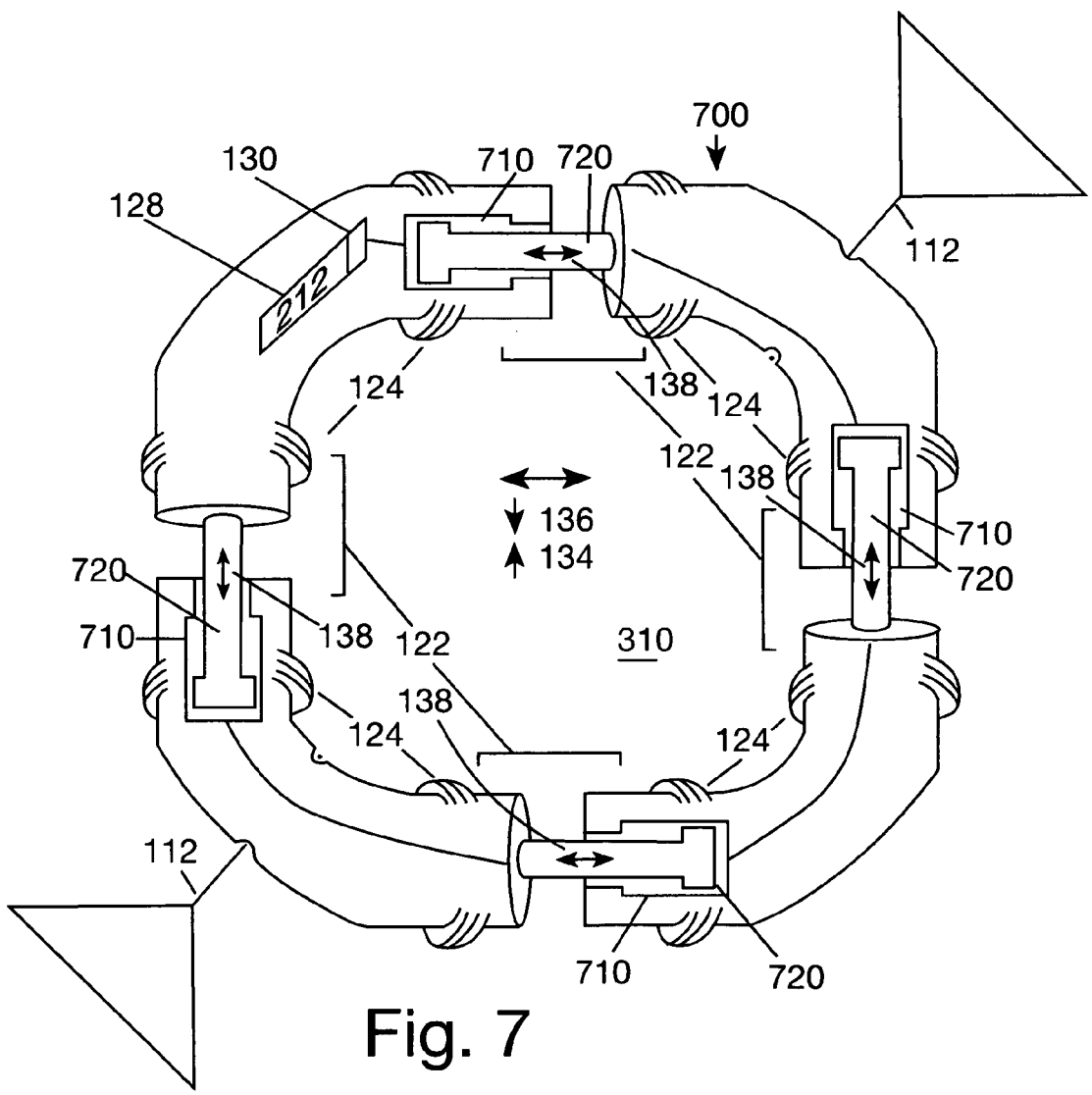

To provide variable diameters in a torus, there are many alternative mechanisms than may be contemplated. Just one alternative variable diameter mechanism is shown in FIG. 7.

A mobile torus 700 comprising hydraulic pistons 720 that are electronically controlled to move in a direction 138 with respect to hydraulic chambers 710, thereby imparting a constant pressure by changing diameter of mobile torus 700. As noted above, a user sets display 128 to provide a constant exsanguinating pressure to extremity 310.

Inflatable Ballast Mobile Torus

In addition to sections that telescope in order to provide changes in diameter, there are other options that vary stiffness and/or tension throughout the torus to provide constant exsanguination pressure.

Figure 8:
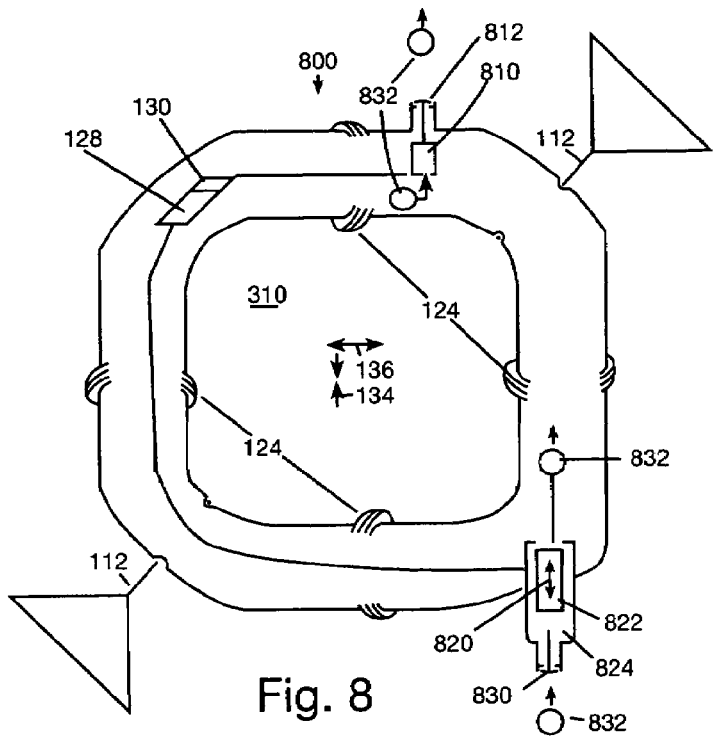
FIGS. 8 and 9A-B show configurations of an inflatable mobile torus, according to embodiments of the invention.

One example of variable stiffness and/or tension through a torus is shown in FIG. 8 in which an inflatable ballast mobile torus 800 comprising an electronically controlled inflation pump 824 having an inlet 830 and a pump piston 822 that moves in directions 820 to draw a fluid 832 into inlet 830 and onto inflatable ballast mobile torus 800.

With intake of fluid 832, pressure within inflatable ballast mobile torus 800 increases, reducing the diameter across the inner portion of inflatable ballast torus 800, thereby maintaining constant pressure over a small diameter extremity portion.

Optionally, inflatable ballast mobile torus 800 maintains a tension, for example by varying stiffness due to increased pressure therein, that adjusts to the various diameters around the extremity.

As inflatable ballast torus 800 passes over an extremity portion having a larger cross section, an electronically controlled deflation pump 810 opens a valve 812 that releases fluid 832. According to some embodiments of the invention, fluid 832 comprises a gas, for example nitrogen or environmental air. In other embodiments, fluid 832 comprises a liquid.

While the mobile torus examples described have been described with wheels 124 to facilitate movement, embodiments without wheels are contemplated as well as additional constant pressure-providing mechanisms; one such possible configuration incorporating these embodiments being described as follows:

Self-Contained Inflatable Ballast Torus

Figure 9A:
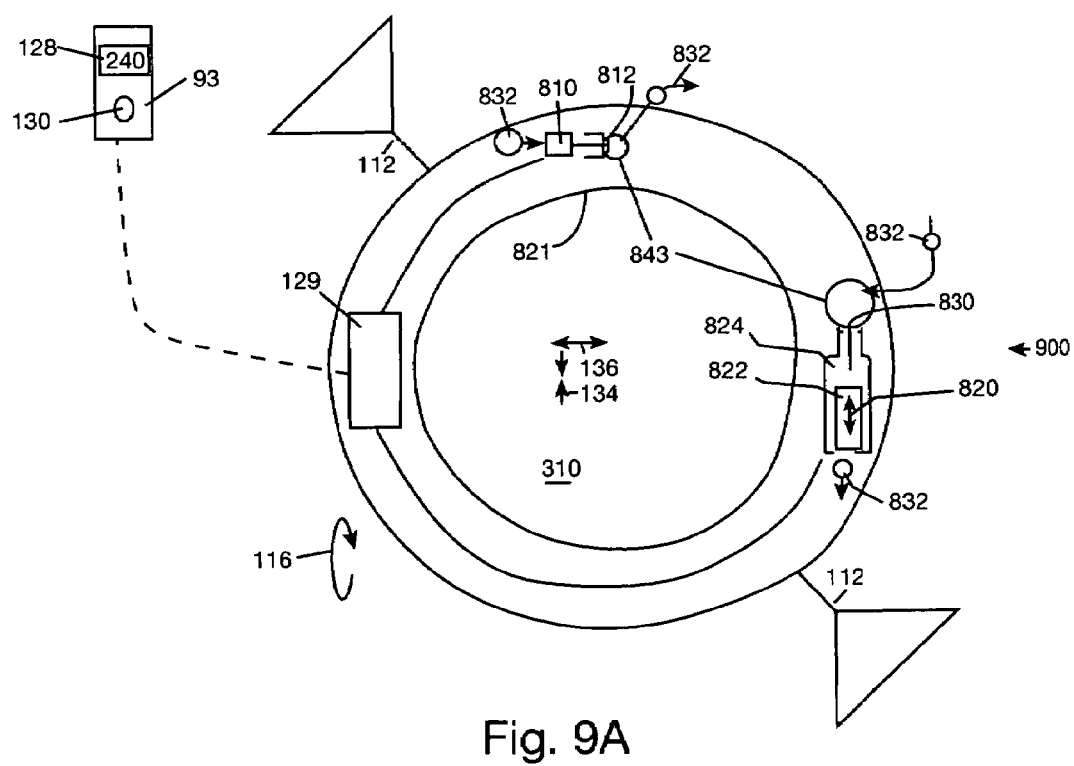

An inflatable torus is not limited to an intake that extends from the torus, but may comprise an external fluid source that is taken into openings that are flush with the torus. One example of fluid source intake that is flush with the torus is a self-contained inflatable ballast torus 900 shown in FIG. 9A.

Self-contained inflatable ballast torus 900 comprises electronically controlled inflation pump and electronically controlled deflation pump 810 which are contained within inflatable ballast torus 900 and exchange fluid 832 through ports 843 to adjust pressure and change the diameter of self-contained inflatable ballast torus 900.

According to some embodiments of the invention, self-contained inflatable ballast torus 900 includes a substantially friction-free surface 821 that either alone or with a lubricant applied to extremity 310, slides along extremity 310 as handles 112 are pulled.

According to some embodiments of the invention, display 128 is located on a wireless control 93 to adjust inflation pressure on an internally contained wireless inflation controller 129.

With internally contained, herein self-contained, inlet 830, outlet 810, gas 832 and wireless controller 129, stationary self-contained inflatable ballast torus 900 can be twistingly rotated in a direction 116 during movement along extremity 310.

Self-contained inflatable ballast torus 900 may additionally be used as a stationary tourniquet that is secured around extremity 310 after an operator has applied an elastic bandage in a spiral fashion around the extremity in the fashion noted above.

While constant pressure fluid torus embodiments that communicate with the environment have been described, the present invention also contemplates constant pressure torus embodiments in which the fluid pressure is substantially contained within the torus; some of the many possible configurations being described as follows:

Self-Contained Compressed Gas Torus

Figure 9B:
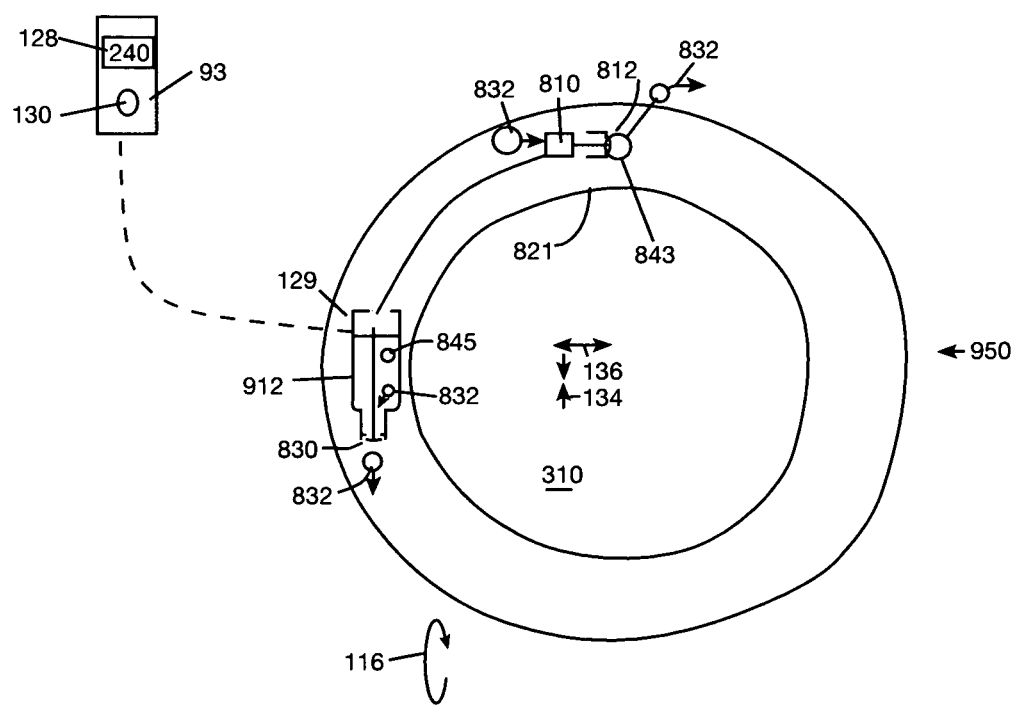

An inflatable torus is not limited to an external fluid source. One example of an internally contained fluid source is shown in FIG. 9B comprising a self-contained inflatable ballast torus 900 which includes a gas bottle 912 containing compressed fluid 832 comprising a compressed gas.

According to some embodiments of the invention, gas bottle 912 can be refilled with the compressed gas through a charging port 845.

Self-contained gas torus 950 can be twistingly rotated in a direction 116 during movement along extremity 310 or may be used as a stationary tourniquet in the above-noted manner.

While constant pressure fluid torus embodiments have been described, the present invention also contemplates constant pressure torus embodiments in which materials of the torus are configured to provide constant pressure; some of the many possible configurations being described as follows:

Varied Fiber Embodiments

In some embodiments, the torus may utilize self actuating fuse fiber mechanisms that respond to changes in pressure by breaking above a specific threshold tension, thereby allowing tighter fuse fiber mechanisms to provide additional pressure to the torus.

One example of a self actuating fuse fiber mechanism is shown in FIGS. 10A-12B in which a varied fiber torus 1000 comprising bands of fibers 110, 120 and 130. As shown in FIGS. 10A and 10B, as varied fiber is twistingly rotated in direction 116 along a narrow extremity portion, all fibers 110, 120 and 130 remain intact, maintaining the small diameter in varied fiber torus 1000.

As shown in FIGS. 11A and 11B, as varied fiber torus 1000 passes along a medium thick extremity, for example portion below the knee around the calf, fibers 110 break and fibers 120 and 130 stretch to maintain constant exsanguination pressure.

As shown in FIGS. 12A and 12B, as varied fiber torus 1000 passes along a larger extremity portion, for example above the knee while approaching the thigh, fibers 120 break. Fibers 130 now stretch along to maintain constant exsanguination pressure.

In further embodiments, varied fiber torus 1000 may be slid by an operator along the extremity in direction 114. In still further embodiments, shown in FIGS. 12C and 12D, varied fiber torus 1000 includes wheels 124 that rotate along extremity 310, as noted above, while being pulled by handles 112.

While constant pressure variable fibered materials can, as describe above, provide constant pressure, there are still further configurations comprising multiple interactive section that can provide constant pressure; one of the many possible configurations includes a plurality of telescoping sections that telescope with respect to cross sections diameters along the torus.

Diaphragm Torus

Figure 13A:
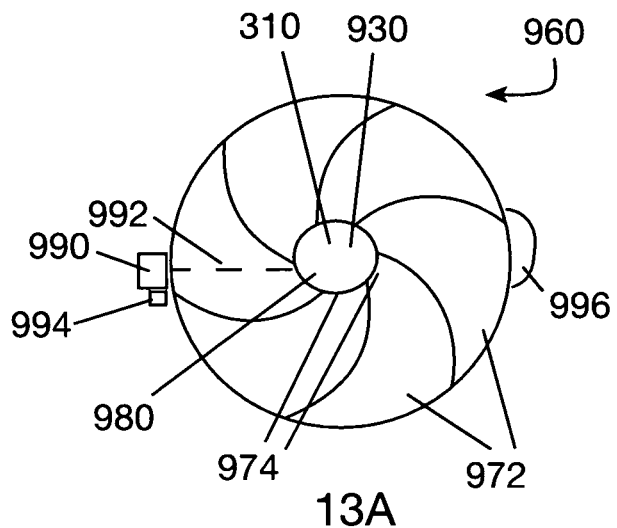
FIGS. 13A-13C show a diaphragm torus, according to embodiments of the invention.

FIG. 13A shows a diaphragm torus 960 comprising moveable sections 972 arranged in a circular pattern surrounding extremity 310. An aperture 980, formed by relative movement between moveable sections 972, is relatively small in order to apply exsanguinating pressure around an ankle 930.

Figure 13B:
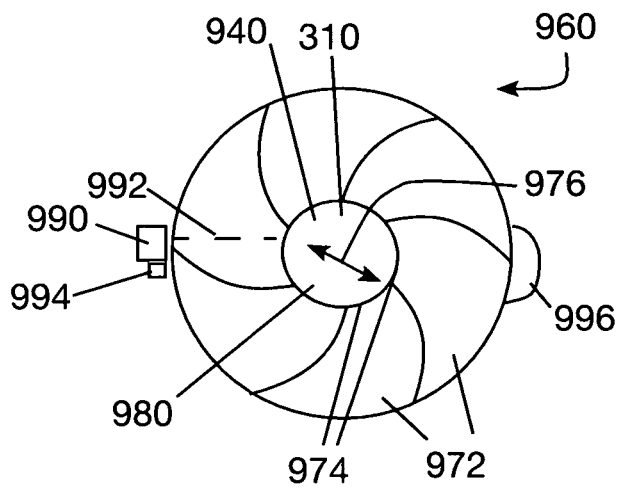

FIG. 13B shows diaphragm torus 960 in which bases 974 of moveable sections 972 have moved apart in a direction 976 to increase the size of aperture 976 thereby maintaining constant exsanguination pressure around a knee 940.

Figure 13C:
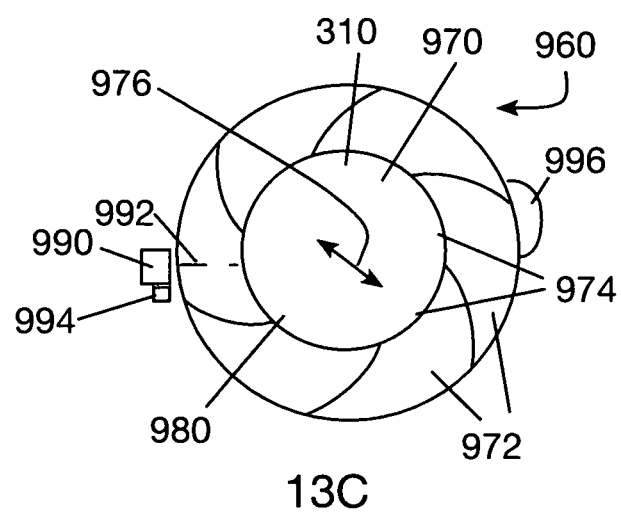

FIG. 13C shows bases 974 having moved further in direction 976 to increase the size of aperture while maintaining the same exsanguinating pressure around a thigh 970.

In embodiments, a distance sensor 990 reflects beams of radiant energy, for example light, laser or ultrasound, to determine the distance to extremity 310 from one or more points around diaphragm torus 960. When distance sensor 990 detects a decreasing distance to extremity 310, for example as torus diaphragm 960 passes from knee 940 to thigh 970 of extremity 310, (FIGS. 13b-13C) distance sensor activates a moveable section transducer 994. Moveable section transducer 994 causes moveable section 972 to move in direction 976 to increase the size of aperture 980, thereby maintaining constant pressure.

In alternative embodiments, a moveable section transducer 996 senses the tension between moveable sections 972 and adjusts the size of aperture 980 in order to maintain constant pressure as the thickness of extremity 310 changes; the many methods of sensing and modifying pressure in diaphragm torus 960 being well-known to those familiar with the art.

Diaphragm torus 960 may be equipped with wireless control 93 to adjust inflation pressure (FIG. 9B). Additionally or alternatively, diaphragm torus 960 may be equipped multiple wheels 124 (FIG. 1) or wheels 670 that are powered by motors 672 (FIG. 6). The many ways in which diaphragm torus 960 can be modified are well-known to those familiar with the art.

It is expected that during the life of this patent many relevant materials and designs for mobile torus exsanguination devices will be developed and the scope of the term "mobile torus exsanguination devices" is intended to include all such new technologies a priori.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for exsanguinating a portion of an extremity, the device comprising:
    i) a torus having a variable circumferential diameter, said torus configured to encircle an extremity portion and apply exsanguination pressure thereto wherein said torus comprises an elastic material and a variably extendable tension band contained by said elastic material; and
    ii) a transducer operatively associated with said torus, wherein said transducer, comprises the at least one variably extendable tension band substantially contained within a cross sectional portion of said torus; said transducer, while said torus is encircling said extremity portion, being configured to control at least one of:
    a diameter of said variable circumferential diameter;
    a tension in said tension band within said torus; and
    a pressure applied by said torus;
    wherein said torus is adjusted actively by said transducer and also passively as said elastic material is compressed against said extremity portion; and
        wherein, said torus includes at least one wheel located around a cross sectional section of an annular portion of said torus, said at least one wheel configured to roll as said torus moves linearly along said extremity portion.

2. The device according to claim 1, wherein during moving of said torus, said transducer is configured to apply a substantially constant exsanguinating pressure to said extremity portion.

3. The device according to claim 1, wherein said torus is configured to move along said extremity portion with at least one of:
    twisting rotation; and
    sliding.

4. The device according to claim 1, wherein said torus is configured to move under power applied from a power source that is external to said at least one wheel.

5. The device according to claim 4, wherein said power source is comprises a manual power source.

6. The device according to claim 1, wherein said torus is configured to move under power applied from a power source that is internal to said at least one wheel.

7. The device according to claim 6, wherein said power source is comprises motorized power source.

8. The device according to claim 1, wherein an outer surface of said at least one wheel comprises at least two projections configured to contact at least a portion of said extremity portion.

9. The device according to claim 1, wherein said at least one wheel, comprises at least two wheels: one first wheel configured to slidingly engage at least one second wheel.

10. The device according to claim 1, wherein said torus includes at least one handle configured to provide at least one of:
    pulling said torus along said extremity portion; and
    guiding said torus along said extremity portion.

11. The device according to claim 10, wherein said at least one handle is rotatably connected to said torus.

12. The device according to claim 1, wherein said transducer comprises at least two bands of fibers at least partially encircling said torus, said at least two bands of fibers comprising:

at least one first band of fibers having a first rate of elasticity; and at least one second band of fibers having a second rate of elasticity.

13. The device according to claim 12, wherein:

said at least one first band of fibers break when stretched above said first rate of elasticity; and said at least one second band of fibers break when stretched above said second rate of elasticity.

14. The device according to claim 12, wherein said torus includes at least one handle configured to provide at least one of:

pulling said torus along said extremity portion; and guiding said torus along said extremity portion.

15. The device according to claim 14, wherein said torus includes at least one motor configured to propel said torus during moving of said torus.

16. The device according to claim 1, wherein said transducer includes a tension controller including a tension level input.

17. The device according to claim 16, wherein said tension level input comprises a wireless transceiver configured to receive and transmit wireless tension-based signals.

18. The device according to claim 1, wherein said torus includes at least one pulling handle configured to pull said torus along said extremity portion.

19. The device according to claim 18, wherein said torus includes at least one motor configured to propel said torus during moving of said torus.

20. A method for exsanguinating an extremity portion, the method comprising:

i) providing a torus configured to encircle a cross sectional annulus of an extremity portion; wherein said torus comprises:

an elastic material; and one variable circumferential diameter adjuster, having a variable coefficient of tension comprising at least one of:

a variable length band; and a variably inflatable ballast;

substantially contained within a cross sectional portion of said torus, configured to apply substantially constant exsanguinating pressure to said extremity portion;

ii) moving said torus along said extremity portion; and iii) applying said substantially constant exsanguinating pressure with said torus to said extremity during said moving as said elastic material is compressed against said extremity and by increasing the tension in said circumferential diameter adjuster to decrease the diameter of said torus as it is moved over narrower cross-sections of said extremity and decreasing the tension in said circumferential diameter adjuster to increase the diameter of said torus as it is moved over wider cross-sections of said extremity.

21. The method according to claim 20, wherein said circumferential diameter adjuster comprises multiple sections comprising at least one of:

at least two fibers having differing rates of elasticity; and at least two sections of a diaphragm.

22. The method according to claim 20, wherein said moving of said torus along said extremity portion comprises at least one of:

twisting rotation;

rolling; and sliding.

* * * * *